United States Patent [19]

Lazarus

[11] Patent Number: 4,886,500
[45] Date of Patent: Dec. 12, 1989

[54] EXTERNAL GUIDE WIRE

[76] Inventor: Harrison M. Lazarus, 853 13th Ave., Salt Lake City, Utah 84103

[21] Appl. No.: 270,661

[22] Filed: Nov. 7, 1988

[51] Int. Cl.$^4$ .................. A61M 5/00; A61M 25/00
[52] U.S. Cl. .................................... 604/164; 128/272; 128/657
[58] Field of Search .............. 604/164, 158, 170, 280; 128/772, 656–658

[56] References Cited

U.S. PATENT DOCUMENTS

| | | | |
|---|---|---|---|
| 3,731,671 | 5/1973 | Mageoh | 604/95 |
| 4,553,960 | 11/1985 | Lazarus et al. | 604/158 |
| 4,830,023 | 5/1989 | de Toledo | 128/657 |

Primary Examiner—Stephen C. Pellegrino
Attorney, Agent, or Firm—Trask, Britt & Rossa

[57] ABSTRACT

A guide wire for insertion into a patient has a tapered distal end and is positioned around the exterior of a trocar for positioning within a patient. The wire has a separation section and two portions. A kit includes the wire and a cannula for emplacement in a patient.

12 Claims, 2 Drawing Sheets

EXTERNAL GUIDE WIRE

BACKGROUND OF THE INVENTION

1. Field

This invention relates to medical apparatus, and more particularly to guide wires that are placed inside the body to guide a cannula to a desired position and kits therefor.

2. State of the Art

Today many different kinds of cannulas are inserted into patients for administering a wide variety of therapies. For example, a catheter of the type which is comprised of a trocar and a cannula may be inserted into a blood vessel to, for example, administer different fluids including whole blood, salt solution, and other therapeutic liquids through the cannula after removal of the trocar. The catheter may also be used to place instruments and to remove blood. U.S. Pat. No. 4,553,960 (Lazarus et al.) illustrates and describes a peritoneal lavage procedure employing a catheter and a cannula inserted into the peritoneal cavity.

In some instances, it is desirable to position a fairly large cannula within the body in a particular position or location. Positioning of such a large cannula through the skin can be difficult. Similarly, it may be difficult to direct the larger cannula to the appropriate or desired location within the body. Accordingly, today a guide wire may be prepositioned to guide the larger cannula. That is, a small trocar may be used to penetrate the skin and desirably to position a small diameter cannula in a desired location. After removal of the trocar, a guide wire is inserted through the in-place cannula and directed further interior the patient through, for example, a blood vessel. The cannula may then be removed over the guide wire and the larger cannula slid over the guide wire to follow the guide wire through the body to the desired location. U.S. Pat. No. 4,553,960 (Lazarus et al.) illustrates another use of such a guide wire. U.S. Pat. No. 4,545,390 (Leary) also describes use of a guide wire. U.S. Pat. No. 4,534,363 discloses a special form of guide wire.

The guide wires heretofore known are spring wound and similar in structure to piano wire. In some instances, they have varying diameters between a distal or interior end and an exterior or proximal end. Such wires are typically sized to be positioned through the interior of small cannulas and in a fashion similar to that illustrated in U.S. Pat. No. 4,553,960. In some instances, a hollow needle may be used without a cannula. That is, the hollow needle is inserted into the patient after which a guide wire is inserted through the hollow needle.

No guide wire has yet been suggested which in use would minimize the number of procedural steps associated with the positioning of a large catheter or minimize the steps associated with the cannulation of a patient when a guide wire is used.

SUMMARY OF THE INVENTION

A guide wire is provided for use with a needle-like device which is used to penetrate a patient. The needle-like device has structure extending from a hub. The guide wire has a body with a lumen sized and shaped to slidably and snugly adapt about the structure to extend from a distal end proximate the tip of the structure to a proximal end outside the body of a patient with the structure positioned into the patient. A tip is formed at the distal end of the body. The tip is sized and shaped to fair toward the exterior surface of the structure. A separation section is formed in the body and positioned between the distal end and the proximal end. The separation section forms a first and second portion of the body.

In one embodiment, the guide wire is a plurality of side-by-side joined together loops substantially surrounding the trocar. In another embodiment, the body is a plurality of adjacent or contiguous coils.

The separation section may be a coil or loop rotated away from adjacent coils or loops to form an access into the first section. The access also abuts the hub of the structure to inhibit axial movement of the body away from the tip.

Desirably, the tip of the body is conically shaped, extending away from the needle. The wire is desirably stainless steel.

A kit includes penetration structure with a guide wire and a cannula. The guide wire has its first portion positioned about the penetration structure. The cannula is positioned about the second portion of the guide. The penetration structure, guide wire and cannula are included in a kit. The kit may also include preparation materials for performing the emplacement procedure.

BRIEF DESCRIPTION OF THE DRAWINGS

In the drawings, which illustrate the best mode presently contemplated for carrying out the invention.

DESCRIPTION OF THE ILLUSTRATED EMBODIMENT

Figure 1:
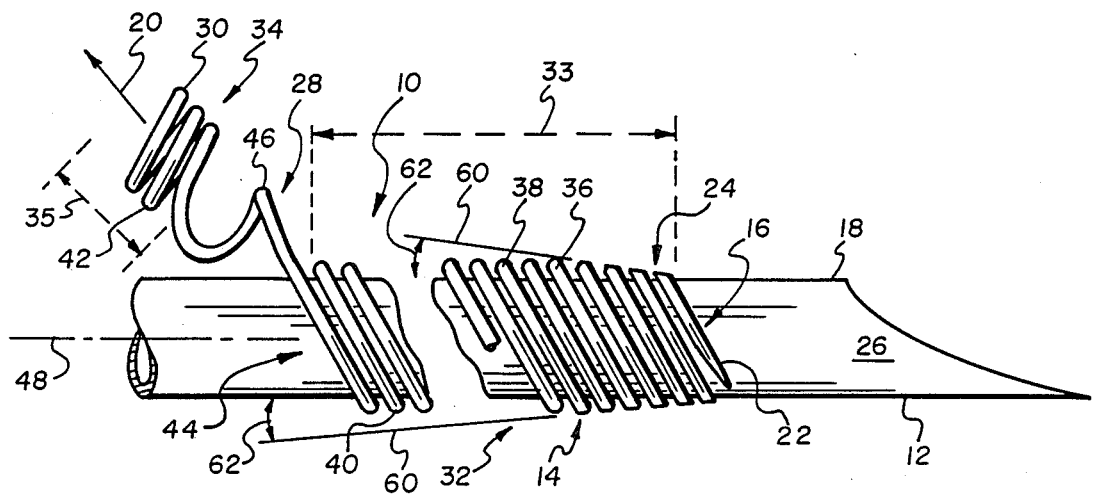
FIG. 1 is an enlarged side view of a guide wire of the invention in position for placement.

Referring to FIG. 1, a guide wire of the instant invention is generally referred to by the numeral 10 and is here shown positioned about a trocar 12 which is similar in structure to the trocar associated with a typical catheter. That is, U.S. Pat. No. 3,352,306 (Hirsch) describes what is today sometimes called a catheter. The catheter of the Hirsch type typically has a sharp hollow needle which may be referred to as a trocar. The trocar is surrounded slidably and snugly by a tube which may be referred to as a cannula. The entire structure has a hub for grasping by the user as known to those skilled in the art. The hub is manipulated to urge the trocar through the skin of a patient to a desired location within the patient such as a blood vessel. A typical catheter is the Angiocath device made by Deseret Medical-Becton Dickinson of Sandy, Utah.

Scalp vein needles and butterfly needles may also serve as the illustrated trocar 12. Indeed, the trocar 12 of FIG. 1 may be, for example, any needle-like device with a stiff or rigid elongate structure to penetrate into the body of a patient.

In FIG. 1, the guide wire 10 includes a body 14. The body 14 has a lumen 16 which is sized and shaped to receive the trocar 12 and to slidably and snugly adapt thereabout. The body 14 extends from proximate the tip 18 of the trocar 12 to outside the body 20 of a patient. The tip 22 of the guide wire 10 at the distal end 24 is formed to fair toward the exterior surface 26 of the trocar 12. By fair, it is meant that it is shaped to diminish in dimension and smoothly blend onto the exterior surface 26 of the trocar 12.

Figure 3:
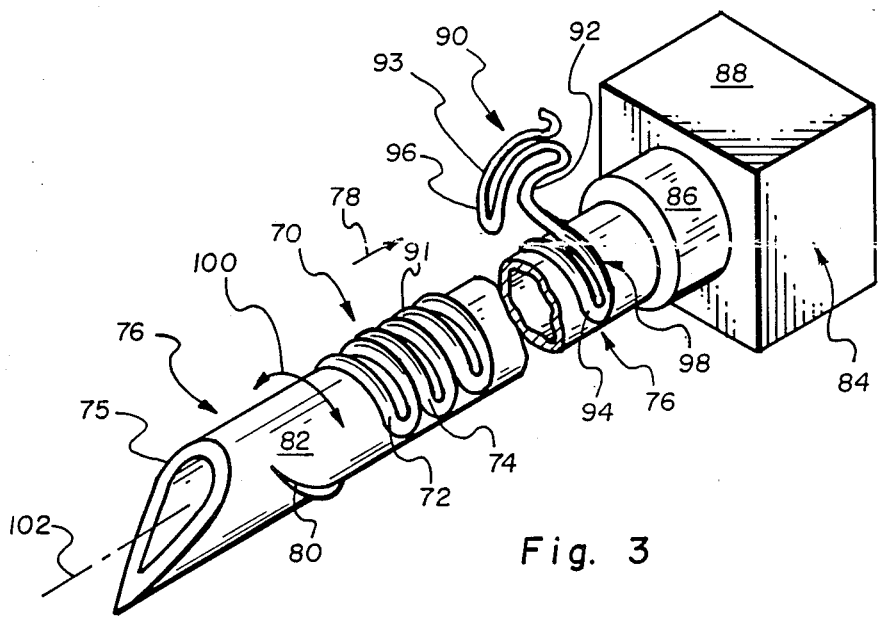
FIG. 3 is an enlarged alternate embodiment of a guide wire of the instant invention.

The guide wire 10 also includes a separation section 28 which is positioned between the distal end 24 and the proximal end 30 of the body 14. The separation section 28 divides the body 14 to form a first portion 32 and a second portion 34. The first portion 32 is sized in length 33 to extend from proximate the tip 18 of the trocar 12 to the hub thereof. The hub of trocar 12 may be any structure intended to remain exterior the patient for grasping or manipulation by the user. A representative hub is illustrated in FIG. 3 and described more fully hereinafter.

The second portion 34 is sized in length to extend from the hub (not shown) a distance selected by the user. The distance contemplated will be the desired additional length of guide wire 10 to be inserted after the trocar 12 with guide wire 10 is inserted into the patient and the distance of a cannula to be inserted over the guide wire 10 with some additional length for manipulation and operation. In actual use, the guide wire 10 may be of different lengths from about 12 inches to as much as two feet. The first section 32 is substantially the length of the trocar 12, which may be from two inches to ten inches. The second section 34 may be from ten inches to about 14 inches. Other lengths may be found suitable by the user based on the desired application.

The separation section 28 is here illustrated to be a coil 46 substantially pulled-apart or rotated with respect to its adjacent coils 40 and 42 to open an access 44 into the lumen 16 of the wire 10 through which the trocar 12 can be readily inserted. The coil 46 is shown elastically deformed although inelastic deformation may be easily effected in many applications.

It may be noted that the access 44 is formed by the coil 46 which is next in sequence to adjacent coil 40. Upon urging the trocar 12 through the skin of a patient, it can be seen that the guide wire first portion 32 will be urged rearward toward the hub (see FIG. 3). The access 44 abuts the hub, precluding or inhibiting actual rearward movement so that the first portion 32 will be urged through the skin along with the trocar 12.

Figure 2:
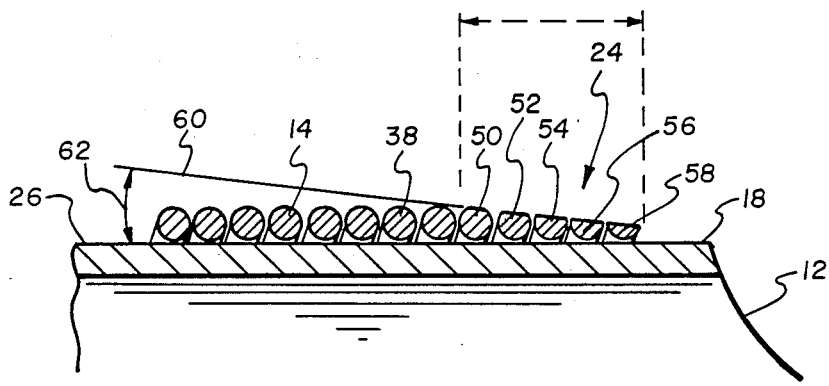
FIGS. 2 and 2A are enlarged partial cross-sectional views of guide wires of the invention.

In FIG. 2, a partial view of the trocar 12 and the body 14 of the guide wire 10 is shown in cross section. The distal end 24 of the body 14 is shown formed to be conical. That is, the coils 50 through 58 are formed to present a substantially or effectively even or smooth surface 60 which extends away from the exterior surface 26 of the trocar at an angle 62. The coils 50-58 are shown with a flat portion which extends about the circumference of each coil to form in effect a conical exterior surface. The angle 62 is selected to reduce the resistance to the guide wire 10 as the trocar 12 with the guide wire 10 is urged through the skin of a patient. It is presently contemplated that the angle 62 will be from about 4 or 5 degrees to about 15 to 20 degrees.

In FIG. 2, it can be seen that the end coil 58 is substantially smaller in cross section than the typical coil such as coil 38. The end of coil 58 is made even smaller in cross section and narrowed, as illustrated in FIG. 1, so that the tip 22 smoothly and snugly fits or fairs against the exterior surface 26 of the trocar 12.

Figure 2A:
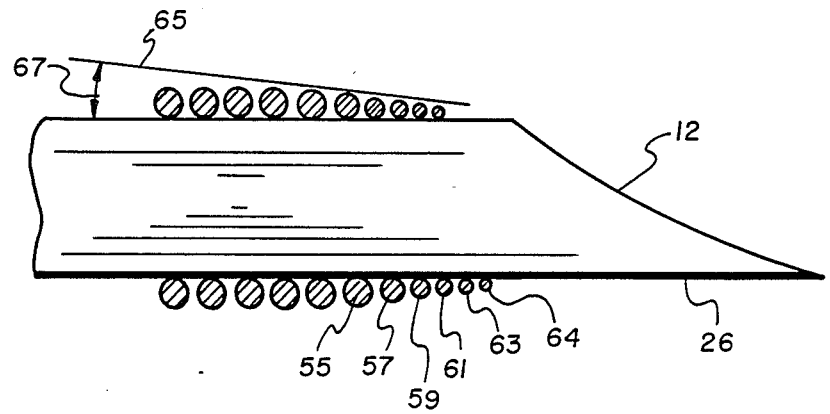

FIG. 2A shows an alternate arrangement in which the coils 55, 57, 59, 61, 63 and 64 are generally round or circular in cross section but of diminishing cross section. A surface 65 around the entire structure is in effect formed to angulate at an angle 67 from the surface 26 of the trocar 12. The surface 65 may be said to be conical and to be faired onto the surface 26 of the trocar 12. The angle 67 is comparable to angle 62 of FIG. 2.

FIG. 3 illustrates an alternate embodiment in which the guide wire 10 is comprised of a body 70 which has a plurality of side-by-side loops joined together. As seen in FIG. 3, the body 70 has a first loop 72 joined to a second loop 74. Each succeeding loop is similarly joined. The loops 72 are a contiguous piece of wire, which form what may be viewed as an unending, continuous series of "s's" extending from the distal end 75 of the trocar 76 to the proximal end 78 not here shown. The tip 80 of the guide wire is faired smoothly onto the surface 82 of the trocar 76 shown in FIG. 3.

The trocar 76 is connected to a hub 84 which has a first section 86 to which the trocar 76 is secured. The hub 84 may also have an enlarged section 88 to facilitate grasping by the user.

The body 70 has a separation section 90 in between a first portion 91 and a second portion 93 which is here shown to be a loop 92 pulled apart from its adjacent loops 94 and 96 and rotated to form an access 98 through which the trocar 76 may be inserted. The loop 92 forms the access 98 which abuts the first portion 86 of the hub 84 to inhibit rearward movement of the first section 91.

It may be appreciated that the loops 72, 74, 94 of the body 70 extend substantially but not entirely about the circumference of the trocar 76. In FIG. 3, the loops 72, 74, 94 of the body 70 extend sufficiently to in effect be held securely on the trocar 76. It is presently contemplated that the loops 72, 74, 94 should extend more than one half the circumference 100 and desirably about 75% of the circumference of the trocar 76. The circumference 100 is the perimeter of the external surface 82 in any section of the trocar 76 taken normal to its axis 102.

Figure 4:
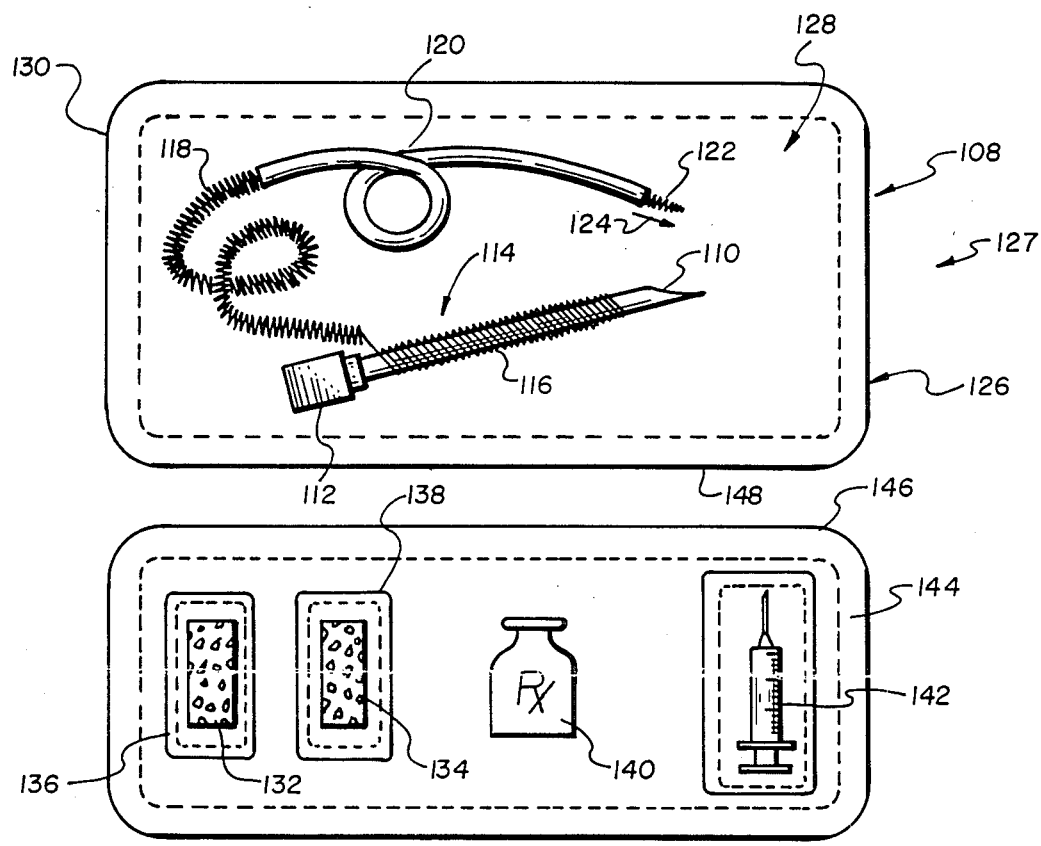
FIG. 4 is a plan view of a kit of the instant invention.

In use, it is expected that the guide wire of the instant invention will be used to effect a cannulation procedure. A kit 108 is illustrated in FIG. 4 to effect such a procedure. More particularly, FIG. 4 shows a trocar 110 with a hub 112 selected for performing a particular procedure. A guide wire 114 is included with its first portion 116 on the trocar 110 and with its second portion 118 coiled.

A cannula 120 is also shown threaded onto the guide wire 114 with a part 122 of the second portion 118 extending out of the cannula 120 a distance 124 to facilitate grasping by the user (e.g., one to three inches).

The kit 108 also includes packaging means which is any package which may be useful to store the kit in a sterile condition for a period of time. The package 127 here shown has a back portion 126 and a top portion 128 sized to register with the back portion 126 which are sealed together along their outer edges 130. The top portion 128 may be translucent to facilitate recognition of the contents.

The kit 108 may also include other items useful for performing a desired procedure including skin preparation means such as antiseptic sponges 132 and 134 which may each be separately contained in a package 136 and 138. The kit 108 may also contain other items including an anesthetic 140 and a syringe 142 for administering it. The other items 132, 134, 140 and 142 may be contained in a separate page 144 which may be joined to the package 127 along two outside edges 146 and 148 by means providing for easy separation by the user. A perforated joinder is presently contemplated. The kit may also be stored in a disposable tray having recesses sized to receive the various articles of the kit.

It may be appreciated that in operation, the guide wire 10 of the instant invention may be simply placed snugly and slidably about the exterior surface of a trocar or other rigid structure for emplacing the guide wire 10 within the body of the patient to a desired location. The conically shaped surface at the distal end 24 reduces drag and facilitates penetration through the skin and the interior portions of the body while providing sufficient rigidity for the body 14 along the surface 26 of the trocar 12.

After the trocar is positioned within the lumen 16 of the body 14, it is, of course, positioned or advanced through the skin into the patient. Thereafter, the trocar may be removed. Upon removal, the memory of the wire may allow the separation section, and more particularly the separation coil 46, to realign with its neighboring coils 42 and 40. A large cannula may then be readily positioned over the top of the guide wire 10 and manipulated into a proper and desired position within the body of a patient.

It may be appreciated that the description of the illustrated embodiment is not intended to limit the scope of the claims, which themselves recite those features regarded as essential to the invention.

What is claimed is:

1. A guide wire for use with a needle-like device having structure with a tip and a hub to penetrate a patient, said guide wire comprising:
   a body having a lumen sized and shaped to slidably and snugly adapt about the structure of a needle-like device to extend from a distal end proximate the tip of said structure to a proximal end outside the body of a patient with said structure positioned into said patient;
   a tip formed at the distal end of said body sized and shaped to fair toward the exterior surface of said structure; and
   a separation section positioned between the said distal and proximate ends to form a first portion and a second portion of said body, said separation section having means to separate said second portion from said structure.

2. The guide wire of claim 1 wherein said body is a plurality of side-by-side joined together loops substantially surrounding said structure.

3. The guide wire of claim 1 wherein said body is a plurality of adjacent coils.

4. The guide wire of claim 3 wherein said separation section is a coil rotated to open an access through an adjacent coil for positioning said structure through said access, said first portion of said body extending from proximate the tip of said structure to proximate the hub of said needle-like device with said adjacent coil abutting said hub to inhibit movement of said guide wire away from said tip.

5. The guide wire of claim 4 wherein the adjacent coils proximate said tip each have a flat surface to form in effect a conically shaped surface extending away from said tip a preselected distance.

6. The guide wire of claim 5 wherein said body is formed from stainless steel.

7. A guide wire comprising:
   a body having a lumen sized and shaped to fit about a trocar to extend from a distal end proximate the tip of said trocar to a proximal end outside the body of a patient with said trocar positioned in a patient;
   a tip formed at the distal end of said body sized and shaped to fair onto the exterior surface of said needle; and
   a separation section positioned between the said distal and proximal ends to form a first portion and a second portion of said body, said separation section having means to separate said second portion from said trocar.

8. The guide wire of claim 7 wherein said body is a coiled wire.

9. The guide wire of claim 8 wherein said separation section is a coil of said coiled wire rotated to open an access into said first portion, said first portion being sized in length to extend from proximate the tip of said trocar to the hub of the trocar.

10. A cannulation kit comprising:
    penetration structure for insertion through the skin of a patient;
    a guide wire having a body with a lumen sized and shaped to fit about the penetration structure to extend from a distal end proximate the tip of said trocar to a proximal end outside the body of a patient with said penetration structure positioned in a patient, a tip formed at the distal end of said body sized and shaped to fair onto the exterior surface of said penetration structure;
    a separation section positioned between the said distal and proximal ends to form a first portion and a second portion of said body, said separation section having means to separate said second portion from said penetration structure; and
    cannula means positioned about said second portion of said body to extend from proximate said proximal end, said cannula means being sized and shaped to pass along said guide wire into said patient.

11. The cannulation kit of claim 10 further comprising packaging means for containing the penetration structure, the guide wire and cannula means in sterile storage.

12. The cannulation kit of claim 11 wherein said penetration structure has an elonged structure and a hub, wherein said guide wire is a coiled wire and wherein said separation section is a coil of said coiled wire rotated to open an access into said first portion, said first portion being sized in length to extend from proximate the tip of said elongated structure to the hub of the elongated structure

* * * * *